US011278444B2

(12) United States Patent
Robichaud et al.

(10) Patent No.: US 11,278,444 B2
(45) Date of Patent: Mar. 22, 2022

(54) SET OF MANDIBULAR ADVANCEMENT SPLINTS WITH ADJUSTABLE ADVANCEMENT, KIT FOR MANDIBULAR ADVANCEMENT AND METHOD OF ADJUSTING MANDIBULAR ADVANCEMENT USING SAME

(71) Applicant: PANTHERA DENTAL INC., Quebec (CA)

(72) Inventors: Gabriel Robichaud, Quebec (CA); Bernard Robichaud, Quebec (CA)

(73) Assignee: PANTHERA DENTAL INC., Quebec (CA)

( * ) Notice: Subject to any disclaimer, the term of this patent is extended or adjusted under 35 U.S.C. 154(b) by 18 days.

(21) Appl. No.: 16/678,659

(22) Filed: Nov. 8, 2019

(65) Prior Publication Data

US 2020/0069457 A1 Mar. 5, 2020

Related U.S. Application Data

(63) Continuation of application No. 16/339,639, filed as application No. PCT/CA2017/051191 on Oct. 5, 2017.

(Continued)

(51) Int. Cl.
*A61F 5/56* (2006.01)
*A61C 7/36* (2006.01)

(52) U.S. Cl.
CPC ................ *A61F 5/566* (2013.01); *A61C 7/36* (2013.01); *A61F 2005/563* (2013.01)

(58) Field of Classification Search
CPC .. Y10T 24/45524; A44B 11/2592; A61F 5/56; A61F 5/05891; A61F 5/566; A61F 2005/563; A61C 7/36
See application file for complete search history.

(56) References Cited

U.S. PATENT DOCUMENTS 4,559,679 A * 12/1985 Downey .................. A42B 3/08 2/421
6,003,213 A 12/1999 Keller et al.
(Continued)

FOREIGN PATENT DOCUMENTS

CA 2942082 A1 10/2015
WO 0001317 A1 1/2000
(Continued)

OTHER PUBLICATIONS

International Search Report of PCT/CA2017/051191 dated Jan. 10, 2018, 4 pages.

(Continued)

*Primary Examiner* — Keri J Nelson
*Assistant Examiner* — Brant T Bennett
(74) *Attorney, Agent, or Firm* — Brooks Kushman P.C.

(57) ABSTRACT

A set of mandibular advancement splints including a maxillary splint having a maxillary abutment assembly and a mandibular splint having a mandibular abutment assembly. At least one of the maxillary abutment assembly and the mandibular abutment assembly comprises an advancement adjustment structure comprising at least one adjustment spacer removably securable to the corresponding one of the maxillary splint and the mandibular splint. The at least one adjustment spacer has a spacing length defining the mandibular advancement provided by the set of mandibular advancement splints. A set of removable adjustment spacers, a mandibular advancement kit, and a method for adjusting a mandibular advancement produced by a set of mandibular advancement splints are also provided.

20 Claims, 10 Drawing Sheets

Related U.S. Application Data

(60) Provisional application No. 62/404,498, filed on Oct. 5, 2016.

(56) References Cited

U.S. PATENT DOCUMENTS 6,052,875 A 4/2000 Fudaki
6,226,844 B1 5/2001 Lerra et al.
6,604,527 B1 * 8/2003 Palmisano ............... A61C 7/08 128/848
7,430,789 B2 10/2008 Wright
8,079,117 B2 12/2011 Pontaoe
8,677,575 B1 3/2014 Bergstrom
9,326,560 B2 5/2016 Lanez
2012/0227750 A1 9/2012 Tucker
2013/0112210 A1 5/2013 Stein
2014/0326252 A1 11/2014 Quaka et al.
2016/0184129 A1 6/2016 Liptak et al.
2017/0273819 A1 * 9/2017 Shim ....................... A61F 5/566
2018/0353321 A1 12/2018 Veis
2019/0033826 A1 1/2019 Kim et al.
2020/0222227 A1 7/2020 Shim
2021/0205118 A1 7/2021 Kelly

FOREIGN PATENT DOCUMENTS

WO 2013143511 A1 10/2013
WO 2019035516 A1 2/2019

OTHER PUBLICATIONS

Written Opinion of PCT/CA2017/051191 dated Jan. 10, 2018, 6 pages.
International Preliminary Report of PCT/CA2017/051191 completed Jan. 18, 2019, 5 pages.
Extended European Search Report dated May 13, 2020 of European Application No. 17857744.1, 9 pages.
Office Action from U.S. Appl. No. 16/678,659 dated Apr. 5, 2021, 38 pages.
Office Action from U.S. Appl. No. 16/339,639 dated Aug. 11, 2021, 59 pages.

* cited by examiner

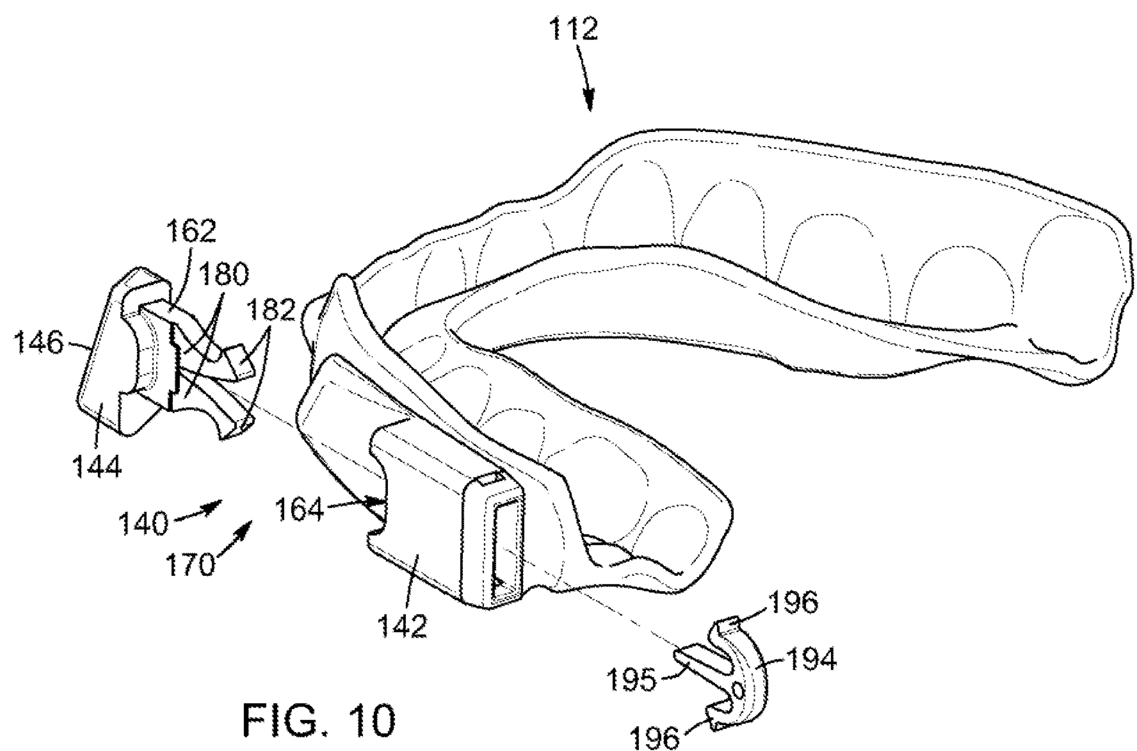
FIG. 10
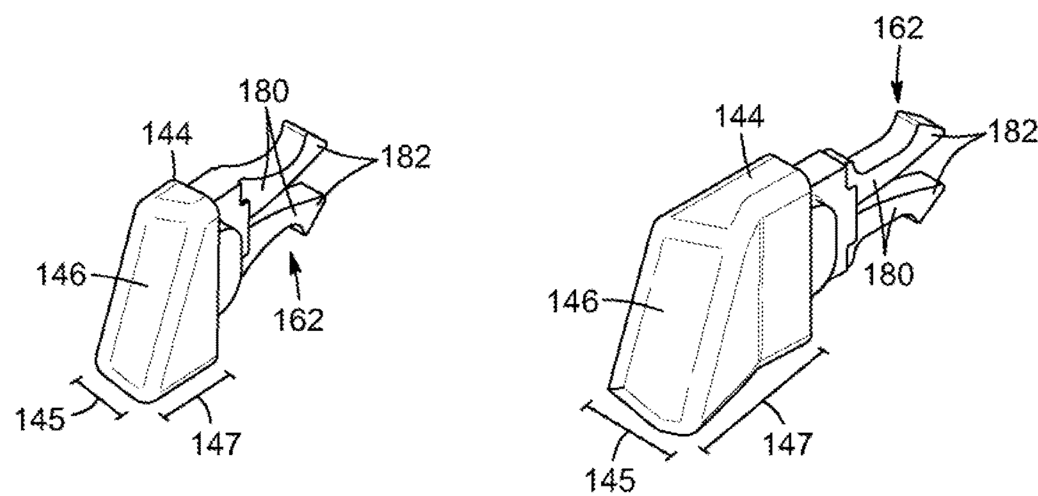
FIG. 11
FIG. 12

SET OF MANDIBULAR ADVANCEMENT SPLINTS WITH ADJUSTABLE ADVANCEMENT, KIT FOR MANDIBULAR ADVANCEMENT AND METHOD OF ADJUSTING MANDIBULAR ADVANCEMENT USING SAME

CROSS-REFERENCE TO RELATED APPLICATIONS

This application is a continuation of a U.S. application Ser. No. 16/339,639, filed on Apr. 4, 2019, which is the U.S. national phase of International Application No. PCT/CA2017/051191 filed on Oct. 5, 2017, which claims priority to U.S. Provisional Patent Application No. 62/404,498 filed on Oct. 5, 2016, the disclosures of which are incorporated in their entirety by reference herein.

TECHNICAL FIELD

The present invention relates to the field of oral devices. More particularly, it relates to an oral device including a two-piece set of occlusal splints cooperating with one another to provide adjustable advancement of a mandible of a patient wearing the oral device, to a set of removable adjustment spacers to be used in combination with the two-piece set of occlusal splints, to a kit for providing the mandibular advancement and to a method for adjusting the mandibular advancement provided by the set of mandibular advancement splints.

BACKGROUND

Several types of oral devices are known in the art to position and maintain the mandible of a patient in a protruded position. For example and without being limitative, such oral devices are commonly used to position and maintain the mandible of a patient in the protruded position during sleep, for instance in the treatment of obstructive sleep apnea.

One type of such oral devices is a two-piece set of occlusal splints, where a maxillary splint and a mandibular splint cooperate to hold a mandible of the patient in the protruded position (i.e. cooperate to advance the mandible of the patient with respect to the maxilla and maintain it in the advanced position). For example and without being limitative, in order to provide the desired mandibular advancement, the maxillary splint and mandibular splint of the set of occlusal splints commonly respectively include complementary maxillary abutment members and mandibular abutment members engageable to position and maintain the maxillary splint and the mandibular splint in a desired mandibular advancement position with regard to one another.

Known sets of occlusal splints however tend to suffer from several drawbacks. For example and without being limitative, in many cases, the position and/or configuration of the mandibular abutment members and maxillary abutment members are fixed, thereby resulting in no adjustment or fine tuning of the occlusal splints, to reach a desired mandibular advancement. In other cases, the configuration and/or position of at least one of the maxillary abutment members and the mandibular abutment members can be varied in a single direction (i.e. the mandibular advancement can be adjusted in a single direction), for example using a unidirectional orthodontic screw allowing a spacing length of an abutment member to be increased, thereby resulting in no possible return to an original position if an adjustment provides an over correction (i.e. a mandibular advancement that is too great).

In view of the above, there is a need for an improved set of occlusal splints, set of removable adjustment spacers to be used in combination with the set of occlusal splints, kit for providing the mandibular advancement and/or method of adjusting the mandibular advancement produced by the set of occlusal splints which would be able to overcome or at least minimize some of the above-discussed prior art concerns.

SUMMARY

According to a first general aspect, there is provided a set of mandibular advancement splints. The a set of mandibular advancement splints comprises: a maxillary splint having a maxillary body with an inner portion adapted to fit a maxillary dental arch of a mouth of a patient and an opposed outer portion having an outer wall surface, the maxillary splint having a maxillary abutment assembly; and a mandibular splint having a mandibular body with an inner portion adapted to fit a mandibular dental arch of the mouth of the patient and an opposed outer portion having an outer wall surface, the mandibular splint having a mandibular abutment assembly. At least one of the maxillary abutment assembly and the mandibular abutment assembly comprises an advancement adjustment structure comprising at least one adjustment spacer removably securable to the corresponding one of the maxillary splint and the mandibular splint. The at least one adjustment spacer has a spacing length defining the mandibular advancement provided by the set of mandibular advancement splints.

In an embodiment, the advancement adjustment structure further comprises at least one support bracket projecting from the outer wall surface of the outer portion of the corresponding one of the maxillary splint and the mandibular splint. Each one of the at least one adjustment spacer is removably securable to a corresponding one of the at least one support bracket.

In an embodiment, each one of the corresponding at least one adjustment spacer and at least one support bracket of the advancement adjustment structure further comprises a complementary male-female connecting assembly for removably securing each one of the at least one adjustment spacer to the corresponding one of the at least one support bracket.

In an embodiment, each one of the at least one support bracket includes a receiving cavity defined therein and protuberances extending into the receiving cavity to define a narrow section thereof. Each one of the corresponding at least one adjustment spacer comprises a protrusion having a distal end and being insertable into the receiving cavity of a corresponding support bracket. The protrusion includes two flexible branches spaced apart from one another and each one of the flexible branches having a stop member defined at the distal end.

In an embodiment, the connecting assembly further comprises a locking member engageable with the protrusion of a corresponding adjustment spacer to lock the adjustment spacer in the support bracket. The locking member includes a locking pin insertable between the two flexible branches of the protrusion of the corresponding adjustment spacer and locking tabs engageable with the support bracket.

In an embodiment, the advancement adjustment structure comprises two adjustment spacers removably securable on opposed sides of the corresponding one of the maxillary splint and the mandibular splint.

In an embodiment, the maxillary abutment assembly comprises the advancement adjustment structure and the mandibular abutment assembly comprises two projections extending upwardly from the outer wall surface, on opposed sides of the mandibular body of the mandibular splint.

In an embodiment, the maxillary abutment assembly comprises lateral support sections. The lateral support sections each are a section of the outer wall surface of the maxillary splint positioned and are configured to abut at least partially with an inner surface of a corresponding adjustment spacer and provide lateral support thereto.

In an embodiment, the outer wall surface of the maxillary splint and the outer wall surface of the mandibular splint each comprise a contact section. The two adjustment spacers and two projections each comprise an abutment surface configured to abut with the abutment surface of a corresponding one of the adjustment spacers and the projections. The maxillary splint and the mandibular splint are configurable in a contact configuration where the contact sections thereof are abutted one against the other along a contact plane. The abutment surface of the two adjustment spacers and two projections at least extend above the contact plane.

In an embodiment, the abutment surface of the adjustment spacers and the abutment surface of the projections have complementary inward inclination.

In an embodiment, the abutment surface of the adjustment spacers has a thickness adapted to the spacing length thereof.

In an embodiment, the at least one adjustment spacer of the advancement adjustment structure is replaceable by at least one adjustment spacer having a different spacing length to vary the mandibular advancement provided by the set of mandibular advancement splints.

In accordance with another aspect, there is also provided a set of removable adjustment spacers removably connectable to a corresponding one of a maxillary splint and a mandibular splint of a set of mandibular advancement splints. Each removable adjustment spacer of the set of removable adjustment spacers comprises a body having a spacing length defining the mandibular advancement provided by the set of mandibular advancement splints and a connecting assembly for removably securing the removable adjustment spacer to the corresponding one of the maxillary splint and the mandibular splint.

In an embodiment, the corresponding one of the maxillary splint and the mandibular splint comprises at least one support bracket projecting from an outer wall surface of an outer portion of the corresponding one of the maxillary splint and the mandibular splint. The connecting assembly of each one of the adjustment spacers is configured to removably secure the adjustment spacer to a corresponding one of the at least one support bracket.

In an embodiment, the connecting assembly comprises one of a male member and a female member for removably securing each one of the at least one adjustment spacer to the corresponding one of the at least one support bracket in a male-female configuration.

In an embodiment, each one of the at least one support bracket includes a receiving cavity defined therein and protuberances extending into the receiving cavity to define a narrow section thereof. Each removable adjustment spacer of the set of removable adjustment spacers comprises a protrusion having a distal end and being insertable into the receiving cavity of a corresponding support bracket. The protrusion includes two flexible branches spaced apart from one another and each one of the flexible branches having a stop member defined at the distal end.

In an embodiment, the connecting assembly further comprises a locking member engageable with the protrusion of a corresponding adjustment spacer, to lock the adjustment spacer in the support bracket. The locking member comprises a locking pin insertable between the two flexible branches of the protrusion of the corresponding adjustment spacer and locking tabs engageable with the support bracket.

In an embodiment, each removable adjustment spacer of the set of removable adjustment spacers has an abutment surface having a thickness adapted to the spacing length thereof.

In accordance with another general aspect, there is also provided a mandibular advancement kit. The mandibular advancement comprises a set of mandibular advancement splints and a kit of adjustment spacers. The set of mandibular advancement splints comprises a maxillary splint having a maxillary body with an inner portion adapted to fit a maxillary dental arch of a mouth of a patient and a mandibular splint having a mandibular body with an inner portion adapted to fit a mandibular dental arch of the mouth of the patient. The kit of adjustment spacers comprises at least two sets of adjustment spacers removably connectable to at least one of the maxillary splint and mandibular splint of the set of mandibular advancement splints. Each set of adjustment spacers includes at least one removable adjustment spacer, each having the same specific spacing length. The spacing length of the at least one removable adjustment spacer is different for each set of adjustment spacers of the kit of adjustment spacers.

In an embodiment, the at least one removable adjustment spacer of each set of adjustment spacers of the kit of adjustment spacers comprises a connecting assembly for removably securing the adjustment spacers to the corresponding one of the maxillary splint and the mandibular splint. The corresponding one of the maxillary splint and the mandibular splint of the set of mandibular advancement splints comprises at least one support bracket projecting from an outer wall surface of an outer portion thereof. The connecting assembly of each one of the adjustment spacers is configured to removably secure the adjustment spacers to a corresponding one of the at least one support bracket.

In an embodiment, the connecting assembly comprises one of a male member and a female member for removably securing each one of the at least one adjustment spacer to the corresponding one of the at least one support bracket in a male-female configuration.

In an embodiment, each one of the at least one support bracket includes a receiving cavity defined therein and protuberances extending into the receiving cavity to define a narrow section thereof. Each adjustment spacer of each set of adjustment spacers comprises a protrusion having a distal end and being insertable into the receiving cavity of a corresponding support bracket. The protrusion includes two flexible branches spaced apart from one another and each one of the flexible branches having a stop member defined at the distal end.

In an embodiment, the connecting assembly further comprises a locking member engageable with the protrusion of a corresponding adjustment spacer to lock the adjustment spacer in the support bracket. The locking member includes a locking pin insertable between the two flexible branches of the protrusion of the corresponding adjustment spacer and locking tabs engageable with the support bracket.

In an embodiment, the corresponding one of the maxillary splint and the mandibular splint to which the at least two sets of adjustment spacers are removably connectable comprises lateral support sections. The lateral support sections each are positioned and configured to abut at least partially with an inner surface of a corresponding adjustment spacer to provide lateral support thereto.

In an embodiment, the adjustment spacers of each set of adjustment spacers have an abutment surface having a thickness. The thickness of the abutment surface of the adjustment spacers of each set of adjustment spacers is adapted to the spacing length thereof. The thickness of the abutment surface of the adjustment spacers having a longer spacing length is greater than the thickness of the abutment surface of the adjustment spacers having a shorter spacing length.

In an embodiment, each set of adjustment spacers includes two adjustment spacers removably securable on opposed sides of the corresponding one of the maxillary splint and the mandibular splint.

In an embodiment, the adjustment spacers of each set of adjustment spacers are connectable to the maxillary splint and the mandibular abutment assembly comprises two projections extending upwardly from the mandibular body, on opposed sides thereof.

In accordance with another general aspect, there is further provided a method for adjusting a mandibular advancement produced by a set of mandibular advancement splints including a mandibular advancement splint and a maxillary advancement splint. The method comprises: engaging a removable adjustment spacer of an initial spacing length to a support bracket of at least one of the mandibular splint and the maxillary splint in a detachable snap-fit engagement through a complementary male-female connecting assembly provided on the adjustment spacer and the support bracket, with the removable adjustment spacer projecting forwardly or rearwardly therefrom, to produce an initial mandibular advancement; and determining if the mandibular advancement is appropriate for the specific patient. If the mandibular advancement is not appropriate for the specific patient, disengaging a previously secured adjustment spacer from the support bracket of the at least one of the mandibular splint and the maxillary splint and successively securing adjustment spacers of different spacing lengths to the support bracket of the at least one of the mandibular splint and the maxillary splint until the mandibular advancement is appropriate.

In an embodiment, the step of successively securing adjustment spacers of different spacing lengths to the at least one of the mandibular splint and the maxillary splint until the mandibular advancement is appropriate includes, if the initial mandibular advancement is insufficient, successively securing adjustment spacers of greater lengths.

In an embodiment, the method comprises the step of reverting to an adjustment spacer of a smaller length if the successive securing of adjustment spacers of greater lengths leads to a mandibular advancement that is too great.

In an embodiment, the step of successively securing adjustment spacers of different spacing lengths to the at least one of the mandibular splint and the maxillary splint until the mandibular advancement is appropriate includes, if the initial mandibular advancement is too great, successively securing adjustment spacers of smaller lengths.

In an embodiment, the method comprises the step of of reverting to an adjustment spacer of a greater length if the successive securing of adjustment spacers of smaller lengths leads to a mandibular advancement that is too small.

In accordance with another general aspect, there is provided a set of mandibular advancement splints comprising: a maxillary splint having a maxillary body with an inner portion adapted to fit a maxillary dental arch of a mouth of a patient and an opposed outer portion having an outer wall surface, the maxillary splint having a maxillary abutment assembly; and a mandibular splint having a mandibular body with an inner portion adapted to fit a mandibular dental arch of the mouth of the patient and an opposed outer portion having an outer wall surface, the mandibular splint having a mandibular abutment assembly. At least one of the maxillary abutment assembly and the mandibular abutment assembly comprises an advancement adjustment structure comprising support brackets projecting outwardly from the outer wall surface of the outer portion of the one of the maxillary splint and the mandibular splint and at least two adjustment spacers selectively and removably securable to a corresponding one of the support brackets. Each one of the support brackets projects from a respective side of the outer portion. The at least two adjustment spacers are removably securable to a corresponding one of the support brackets and project forwardly or rearwardly therefrom when secured to the support brackets. The at least two adjustment spacers and the support brackets further comprise a complementary male-female connecting assembly including a receiving cavity defined in one of the at least two adjustment spacers and the support brackets and a protrusion protruding from the other one of the at least two adjustment spacers and the support brackets, the protrusion being engageable in the receiving cavity in a detachable snap-fit engagement.

In accordance with still another general aspect, there is provided a set of mandibular advancement splints comprising: a maxillary splint having a maxillary body with an inner portion adapted to fit a maxillary dental arch of a mouth of a patient and an opposed outer portion having an outer wall surface, the maxillary splint having a maxillary abutment assembly; and a mandibular splint having a mandibular body with an inner portion adapted to fit a mandibular dental arch of the mouth of the patient and an opposed outer portion having an outer wall surface, the mandibular splint having a mandibular abutment assembly.

At least one of the maxillary abutment assembly and the mandibular abutment assembly comprises an advancement adjustment structure comprising support brackets projecting outwardly from the outer wall surface of the outer portion of the one of the maxillary splint and the mandibular splint, each one of the support brackets projecting from a respective side of the outer portion, and at least two sets of adjustment spacers selectively and removably securable to a corresponding one of the support brackets and projecting forwardly or rearwardly therefrom when secured to the support brackets. The adjustment spacers of a same one of the at least two sets having a same spacing length and the adjustment spacers of different ones of the at least two sets having a different spacing length, the spacing length defining the mandibular advancement provided by the set of mandibular advancement splints having one set of the adjustment spacers secured to the one of the maxillary splint and the mandibular splint.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which:

FIG. 10 is an isometric exploded view of the mandibular splint of the set of occlusal splints of FIG. 6, wherein the advancement adjustment structure is shown with one of the adjustment spacers being disengaged from the corresponding support bracket.

FIG. 11 is an isometric view of one of the adjustment spacers of the advancement adjustment structure of the set of occlusal splints of FIG. 6.

FIG. 12 is an isometric view of one of the abutment spacers of the advancement adjustment structure of the set of occlusal splints of FIG. 6, in accordance with an alternative embodiment where the abutment spacer has a greater spacing length and a greater thickness of the abutment surface.

DETAILED DESCRIPTION

Figure 1:
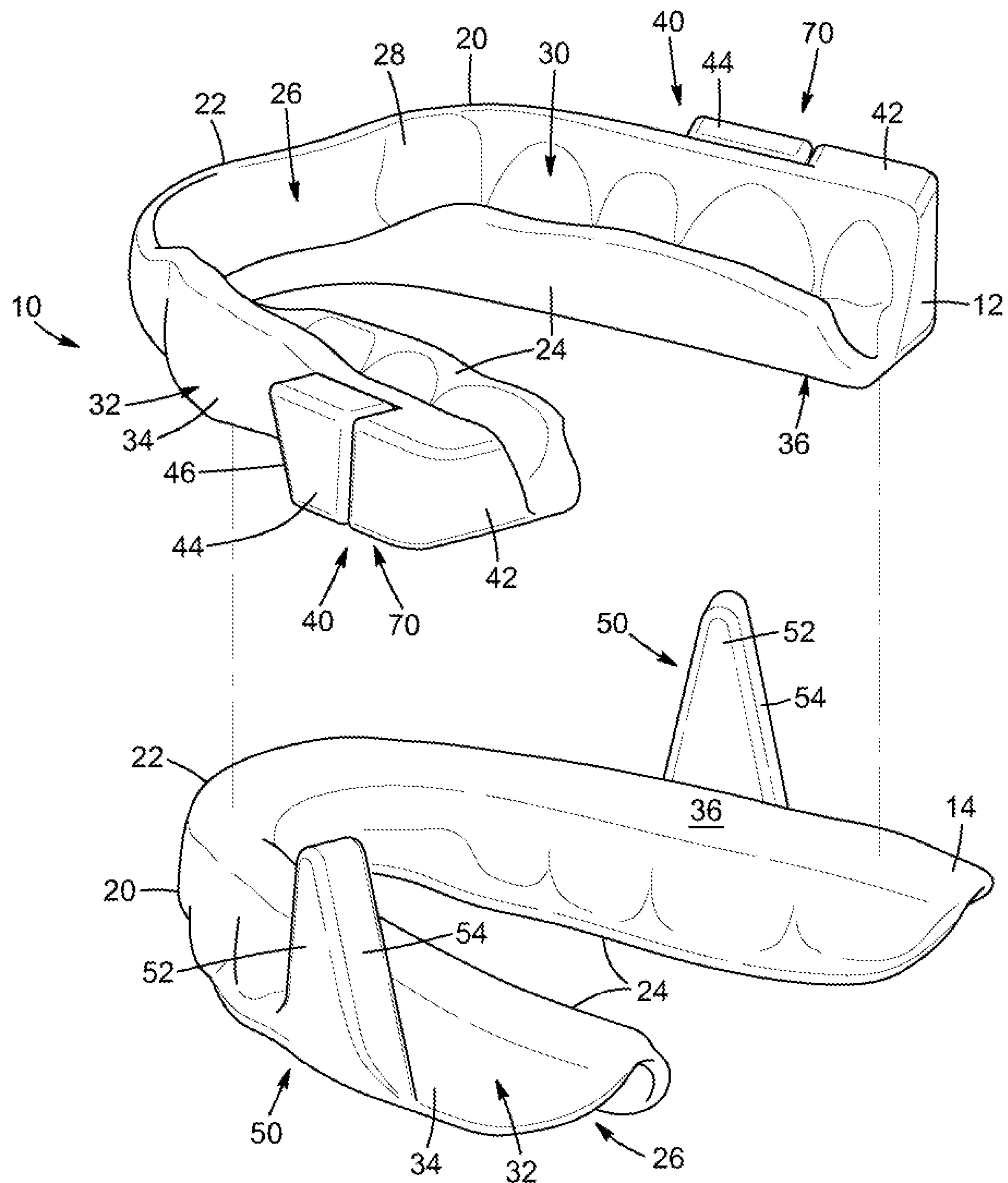
FIG. 1 is a perspective view of a set of occlusal splints, in accordance with an embodiment and wherein the set of occlusal splints includes a maxillary splint and a mandibular splint shown spaced apart from one another.

In the following description, the same numerical references refer to similar elements. The embodiments, geometrical configurations, materials mentioned and/or dimensions shown in the figures or described in the present description are embodiments only, given solely for exemplification purposes.

Although the embodiments of the set of occlusal splints, set of removable adjustment spacers to be used in combination with the set of occlusal splints and/or kit for providing the mandibular advancement and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the set of occlusal splints, as will be briefly explained herein and as can be easily inferred herefrom by a person skilled in the art. Moreover, although the embodiments as illustrated in the accompanying drawings comprise particular steps of a method, not all of these steps are essential and thus should not be taken in their restrictive sense. It is to be understood, as also apparent to a person skilled in the art, that other suitable configurations may be used for the method and system, as will be briefly explained herein and as can be easily inferred herefrom, by a person skilled in the art, without departing from the scope of the invention.

Moreover, it will be appreciated that positional descriptions such as “above”, “below”, “forward”, “rearward” “left”, “right” and the like should, unless otherwise indicated, be taken in the context of the figures and correspond to the position and orientation of the set of occlusal splints and corresponding parts when being worn by a patient, with the “front” corresponding to a position closer to a front of the body of the patient and the “back” corresponding to a position closer to a back of the body of the patient. Positional descriptions should not be considered limiting.

To provide a more concise description, some of the quantitative and qualitative expressions given herein may be qualified with the terms “about”, “substantially”, or the like. It is understood that whether the terms “about” and “substantially” are used explicitly or not, every quantity or qualification given herein is meant to refer to an actual given value or qualification, and it is also meant to refer to the approximation to such given value or qualification that would reasonably be inferred based on the ordinary skill in the art, including approximations due to the experimental and/or measurement conditions for such given value.

According to an embodiment, and as better seen in FIGS. 1 to 4, there is provided a set of mandibular advancement splints 10, comprising a maxillary splint 12 and a mandibular splint 14. The maxillary splint 12 is adapted to fit a maxillary (or superior or upper) dental arch of a mouth of a patient. The mandibular splint 14 is adapted to fit a mandibular (or inferior or lower) dental arch of the mouth of the patient. More particularly, the maxillary splint 12 is engageable over the maxillary dental arch of the patient (not shown) and the mandibular splint 14 is engageable over the mandibular dental arch of the patient (not shown).

Each one of the maxillary splint 12 and the mandibular splint 14 has a substantially U-shaped body 20 (i.e. respectively a maxillary body and a mandibular body), with an anterior section 22 and two posterior sections 24 extending rearwardly from opposite ends of the anterior section 22. The body 20 of each one of the maxillary splint 12 and the mandibular splint 14 has an inner portion 26 (i.e. a section defining an inward part of the corresponding splint 12, 14 for receiving the teeth of the patient) with an inner wall surface 28 defining a teeth receiving cavity 30 configured to encase teeth of the corresponding dental arch. In an embodiment, the inner wall surface 28 of each one of the splints 12, 14 substantially conforms to the shape of the teeth of the corresponding dental arch of the patient. For example and without being limitative, in an embodiment, the shape of the inner wall surface 28 can be designed by scanning a patient’s mouth and designing the inner wall surface 28 to substantially conform to the particular shape of the patient’s teeth obtained by the scan. The body 20 of each one of the maxillary splint 12 and the mandibular splint 14 also has an outer portion 32 (i.e. a section defining an outward part of the corresponding splint 12, 14 and facing a direction opposed to the inner portion 26), and including an outer wall surface 34. For each one of the maxillary splint 12 and the mandibular splint 14, the outer wall surface 34 of the outer portion 32 of each one of the maxillary splint 12 and the mandibular splint 14 comprises a contact section 36.

Figure 2:
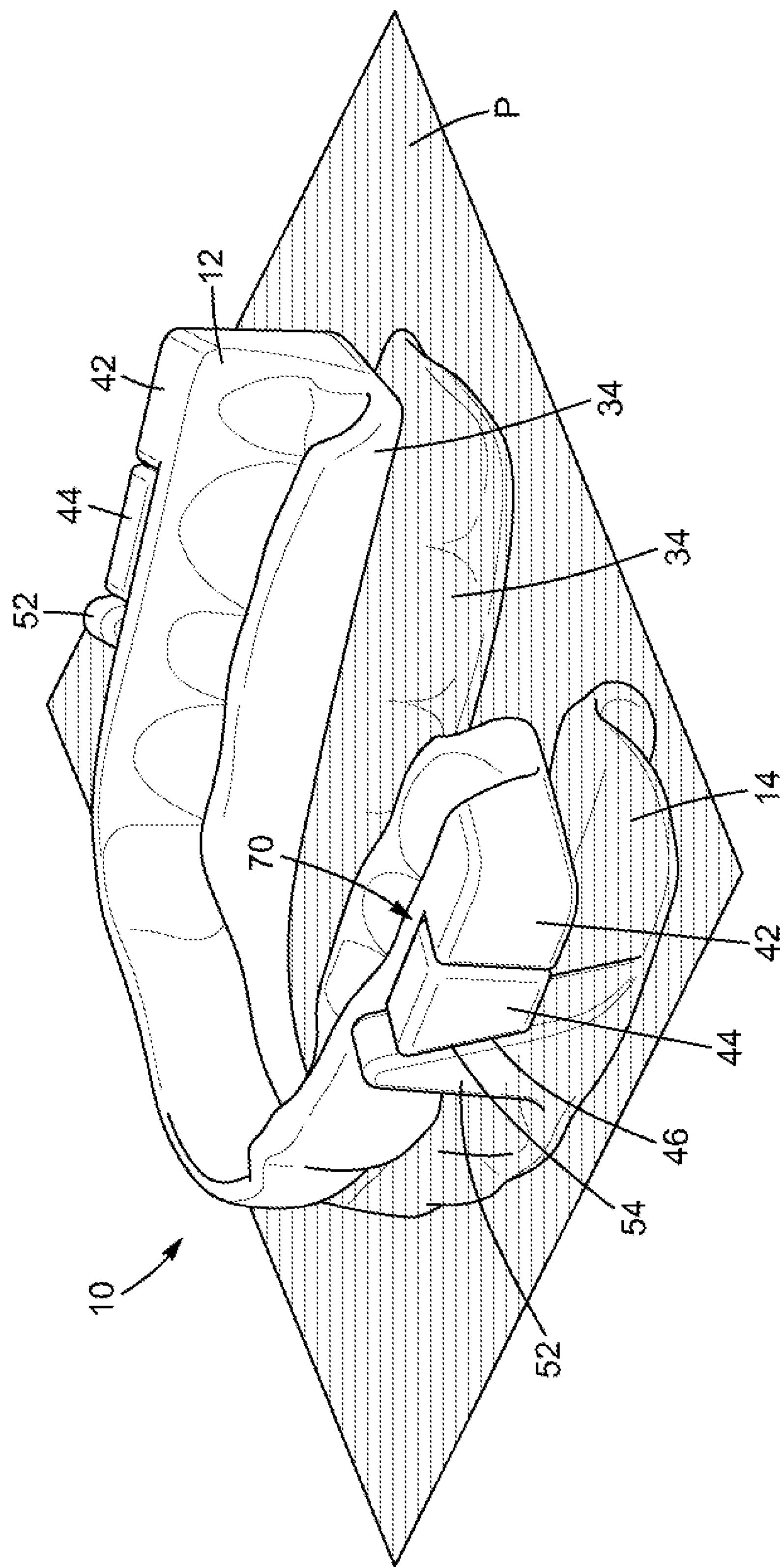
FIG. 2 is a perspective view of the set of occlusal splints of FIG. 1, wherein the maxillary splint and the mandibular splint are shown in a contact configuration.
Figure 3:
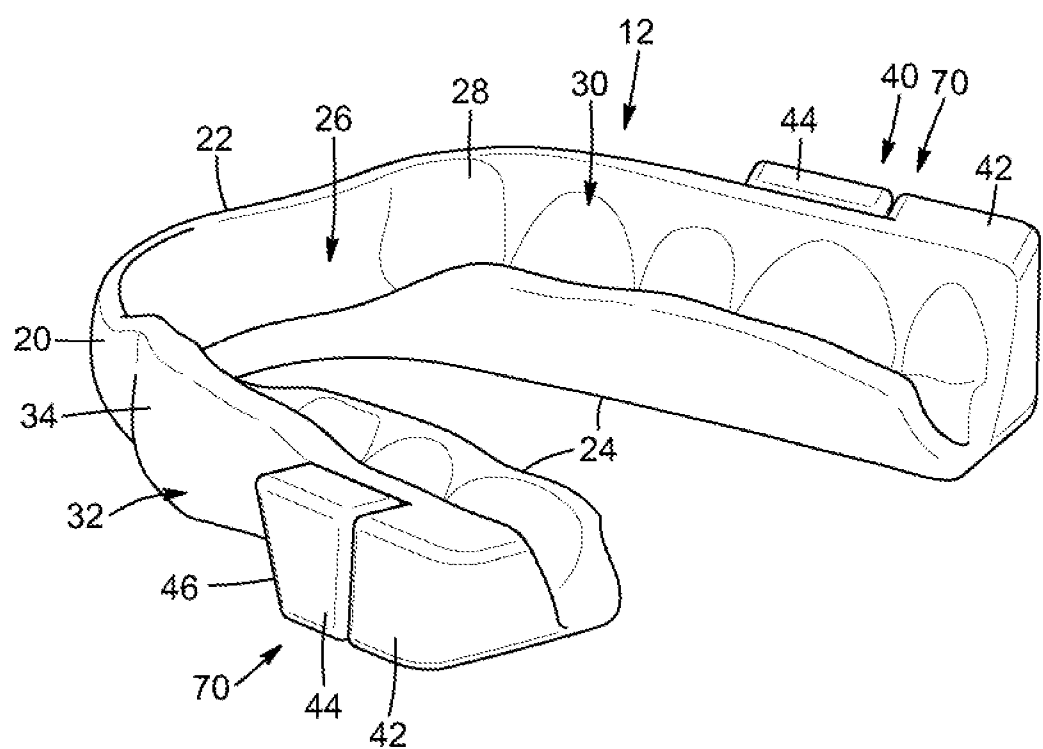
FIG. 3 is a perspective view of the mandibular splint of the set of occlusal splints of FIG. 1, wherein an advancement adjustment structure is shown with two adjustment spacers, each one being engaged with a corresponding support bracket.
Figure 4:
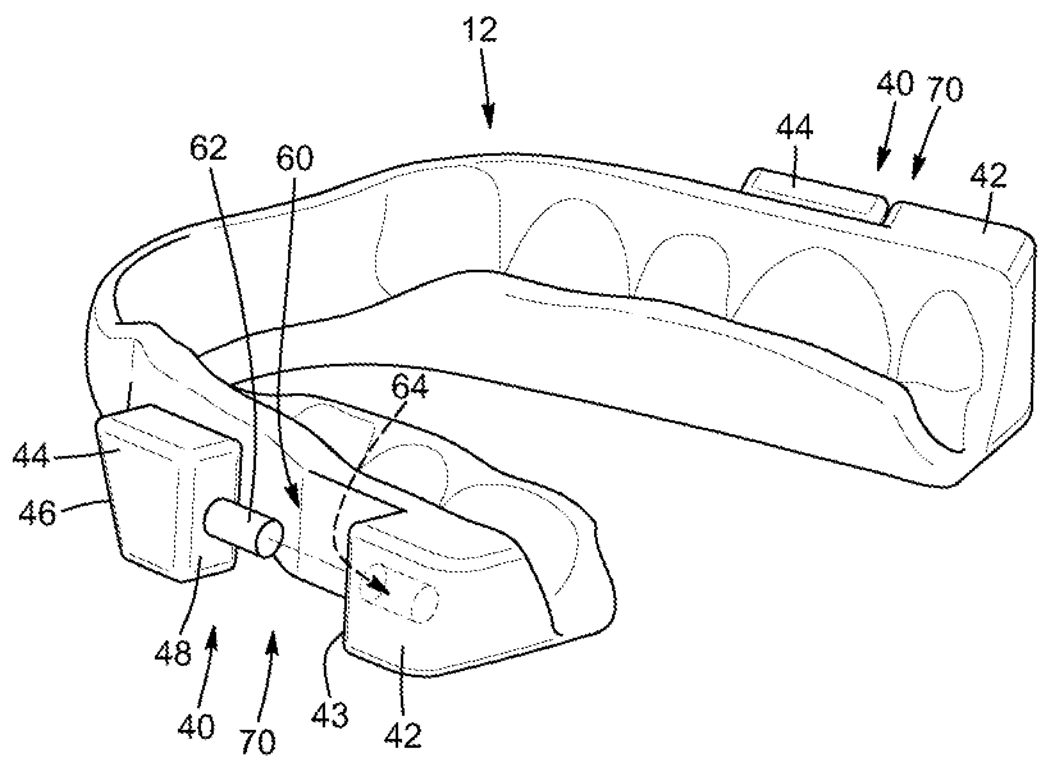
FIG. 4 is an isometric exploded view of the mandibular splint of the set of occlusal splints of FIG. 1, wherein the advancement adjustment structure is shown with one of the adjustment spacers being disengaged from the corresponding support bracket.
Figure 5:
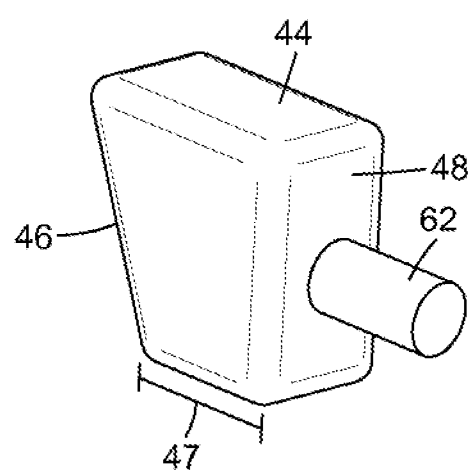
FIG. 5 is an isometric view of one of the adjustment spacers of the advancement adjustment structure of the set of occlusal splints of FIG. 1.

As can be better seen in FIG. 2, the splints 12, 14 are configurable in a contact (or occlusion or clenched) configuration where the contact sections 36 of the outer wall surface 34 of the maxillary splint 12 and the mandibular splint 14 are abutted one against the other. The contact sections 36 are abutted along a contact plane P corresponding to a plane along which the contact sections 36 of the outer wall surface 34 of the maxillary splint 12 and the mandibular splint 14 are substantially aligned when the splints 12, 14 are configured in the contact configuration. In the embodiment shown, the contact sections 36 are planar surfaces (see FIG. 1), (i.e. the outer wall surfaces 34 are substantially flat along the contact plane P, in the contact sections 36). One skilled in the art would however understand that, in alternative embodiments (not shown), the contact sections 36 of the outer wall surfaces 34, can be raised surfaces or complementary uneven surfaces or can even present any other configuration allowing abutment between the splints. In the embodiment shown and as will be described in more details below, when the splints 12, 14 are in the contact configuration, the positioning of the splints 12, 14 relative to one another is modified (i.e. the positioning along a transversal plane of the body of the patient is modified to hold a mandible of the patient in a protruded position).

In the embodiment shown, the contact sections 36 extend along substantially the length of the anterior section 22 and the posterior sections 24, but one skilled in the art will understand that, in an alternative embodiment (not shown), the contact sections 36 can be restricted to only one of the anterior section 22 and the posterior sections 24, or only a portion thereof. In the alternative embodiments (not shown) where the contact sections 36 are limited to only one of the anterior section 22 and the posterior section 24, or a portion thereof, the sections of the anterior section 22 and the posterior section 24 along which the contact sections 36 do not extend can be spaced apart from one another when the splints 12, 14 are configured in the contact configuration.

Now referring to FIGS. 1 to 5, the maxillary splint 12 and the mandibular splint 14 also respectively include a maxillary abutment assembly 40 and a complementary mandibular abutment assembly 50 cooperating to provide the desired mandibular advancement. As can be seen more clearly in FIG. 2, the maxillary abutment assembly 40 and the complementary mandibular abutment assembly 50 are sized and shaped to abut against one another when the splints 12, 14 are configured in the contact configuration and drive the mandibular splint 14 forward to produce the desired mandibular advancement.

In the embodiment shown, the mandibular abutment assembly 50 of the mandibular splint 14 includes two projections 52 extending upwardly from the outer wall surface 34 and positioned on opposite sides of the mandibular splint 14. Each projection 52 extends above the above-described contact plan P (i.e. past the contact section 36 of the outer wall surface 34 of the mandibular splint 14). Each projection 52 is located outwardly of the contact section 36 of the outer wall surface 34 of the mandibular splint 14, thereby not hindering the engagement of the contact sections 36 of the outer wall surface 34 of the maxillary splint 12 and the mandibular splint 14, in the contact configuration. Each one of the projections 52 includes an abutment surface 54 configured to abut with the abutment surface of the components of the maxillary abutment assembly 40, as will be described in more details below. In the embodiment shown, at least a section of the abutment surface 54 of each one of the projections 52 is located above the contact plan P. One skilled in the art will understand that, in an alternative embodiment (not shown), the abutment surface 54 of each one of the projections 52 could extend at least partially below the contact plan P. Moreover, in another alternative embodiment (not shown), each one of the projections 52 could project outwardly of the outer wall surface 34, below the contact plan P, with the abutment surface 54 of each one of the projections 52 being located below the contact plan P.

In the embodiment shown in FIGS. 1 to 5, the maxillary abutment assembly 40 of the maxillary splint 12 includes an advancement adjustment structure 70. In the embodiment shown, the advancement adjustment structure 70 includes two support brackets 42 projecting outwardly from the outer wall surface 34, on opposite sides of the maxillary splint 12, and superposed thereto. In the embodiment shown, the support brackets 42 are integral to the body 20 of the maxillary splint 12. The advancement adjustment structure 70 also includes two adjustment spacers 44. Each one of the adjustment spacers 44 is removably securable to a corresponding one of the support brackets 42. Each one of the adjustment spacers 44 includes an abutment surface 46 at least partially abuttable against the abutment surface 54 of the corresponding projection 52 of the mandibular abutment assembly 50, when the splints 12, 14 are configured in the contact configuration (See FIG. 2). As will be easily understood, when the splints 12, 14 are configured in the contact configuration, abutment between the abutment surfaces 46 of the adjustment spacers 44 and the abutment surfaces 54 of the projections 52 of the mandibular abutment assembly 50 produces the desired mandibular advancement.

In view of the above, it will be understood that, in the embodiment shown, the mandibular advancement provided by the set of mandibular advancement splints 12, 14 is based on a spacing length 47 (which will be defined in more details below) of the adjustment spacers 44 used as part of the advancement adjustment structure 70 of the maxillary abutment assembly 40. Hence, to vary the mandibular advancement provided by the set of mandibular advancement splints 12, 14, the adjustment spacers 44 can be replaced by adjustment spacers 44 having a different spacing length 47, as will be defined and described in more details below.

One skilled in the art will understand that, in alternative embodiments, assemblies different than the embodiment shown can be used for the mandibular abutment assembly 50 and maxillary abutment assembly 40. For example and without being limitative, in an embodiment (not shown), the mandibular abutment assembly 50 could include the advancement adjustment structure 70 (i.e could include a removable member removably connectable to the mandibular splint 14, such as the above described combination of support brackets 42 and adjustment spacers 44), while the maxillary abutment members 40 could include fixed members such as the above described projections 52. In other alternative embodiments (not shown), both the mandibular abutment assembly 50 and maxillary abutment assembly 40 could include an advancement adjustment structure 70. Moreover, each one of the mandibular abutment assembly 50 and maxillary abutment assembly 40 could include a single component abutting with the other one of the mandibular abutment assembly 50 and maxillary abutment assembly 40, rather than the two opposed components of the embodiment shown.

In the embodiment shown in FIGS. 1 to 5, the abutment surface 46, 54 of each one of the adjustment spacers 44 and projections 52 have complementary forward inclinations (or angular orientations). In other words, an upper end of the abutment surfaces 46, 54 of each one of the adjustment spacers 44 and the projections 52 extends forwardly further than a lower end thereof, thereby defining a forwardly angled surface. Such forward angle thereof allows a gradual mandibular advancement when a patient wearing the splints 12, 14, closes its jaws and progressively moves the splints 12, 14 towards the contact configuration. One skilled in the art will however understand that, in alternative embodiments, the abutment surface 46, 54 of each one of the adjustment spacers 44 and projections 52 could have complementary rearward inclinations (or angular orientations) (see FIGS. 6 and 7) or could have substantially no inclination (i.e. could extend substantially vertically) (not shown).

In the embodiment shown in FIGS. 1 to 5, the abutment surface 46 of each one of the adjustment spacers 44 is positioned above the contact plan P to abut with the abutment surface 54 of each one of the projections 52 also being positioned above the contact plan P, when the splints 12, 14 are configured in the contact configuration. One skilled in the art will however understand that, in alternative embodiments (not shown), wherein the abutment surface 54 of each one of the projections 52 extends at least partially below the contact plan P, the abutment surface 46 of each one of the adjustment spacers 44 could similarly extend at least partially below the contact plan P.

In an embodiment, in order to allow replacement (or substitution) of the adjustment spacers 44, each one of the adjustment spacers 44 is removably connected to the corresponding support bracket 42 through a detachable connecting assembly 60. In the embodiment shown, the connecting assembly 60 includes a complementary male-female assembly. For example and without being limitative, in the embodiment shown, each one of the adjustment spacers 44 includes a protrusion 62 (or male member) engageable into a receiving cavity 64 (or female member or socket) defined in a body of the corresponding support bracket 42. In the embodiment shown, the protrusion 62 projects from a posterior wall 48 of the adjustment spacer 44, distal from the abutment surface 46 thereof, and the receiving cavity 64 is opened in an anterior end 43 (or anterior wall in the embodiment shown where the anterior end includes a partial wall) of the body of the support bracket 42. Hence, when the adjustment spacer 44 is secured (or mounted) to the support bracket 42, the protrusion 62 of the adjustment spacer 44 is engaged into the receiving cavity 64 of the corresponding support bracket 42, with the posterior wall 48 of the adjustment spacer 44 engaging the anterior end 43 of the support bracket 42 and the adjustment spacer 44 extending forwardly thereof. In an alternative embodiment, the posterior wall 48 of the adjustment spacer 44 can only partially engage the anterior end 43 of the support bracket 42 when the adjustment spacer 44 is secured to the support bracket 42 (i.e. a section of the posterior wall 48 of the adjustment spacer 44 can be at least partially spaced apart from the anterior end 43 of the support bracket 42 when the adjustment spacer 44 is secured to the support bracket 42). In another alternative embodiment (not shown), the posterior wall 48 of the adjustment spacer 44 can be spaced apart from the anterior end 43 of the support bracket 42 when the adjustment spacer 44 is secured to the support bracket 42.

Figure 6:
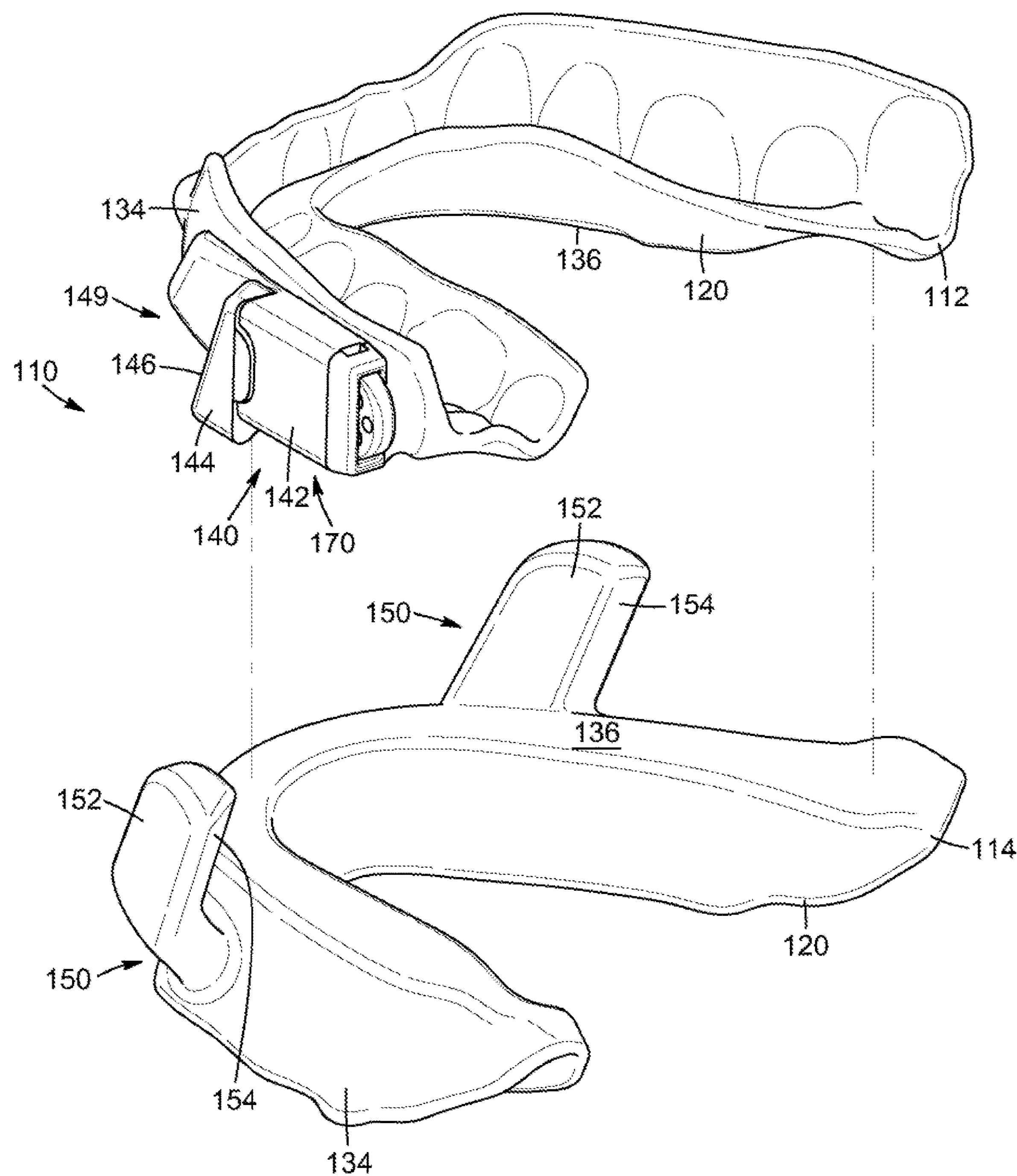
FIG. 6 is a perspective view of a set of occlusal splints, in accordance with an alternative embodiment and wherein the set of occlusal splints includes a maxillary splint and a mandibular splint shown spaced apart from one another.
Figure 7:
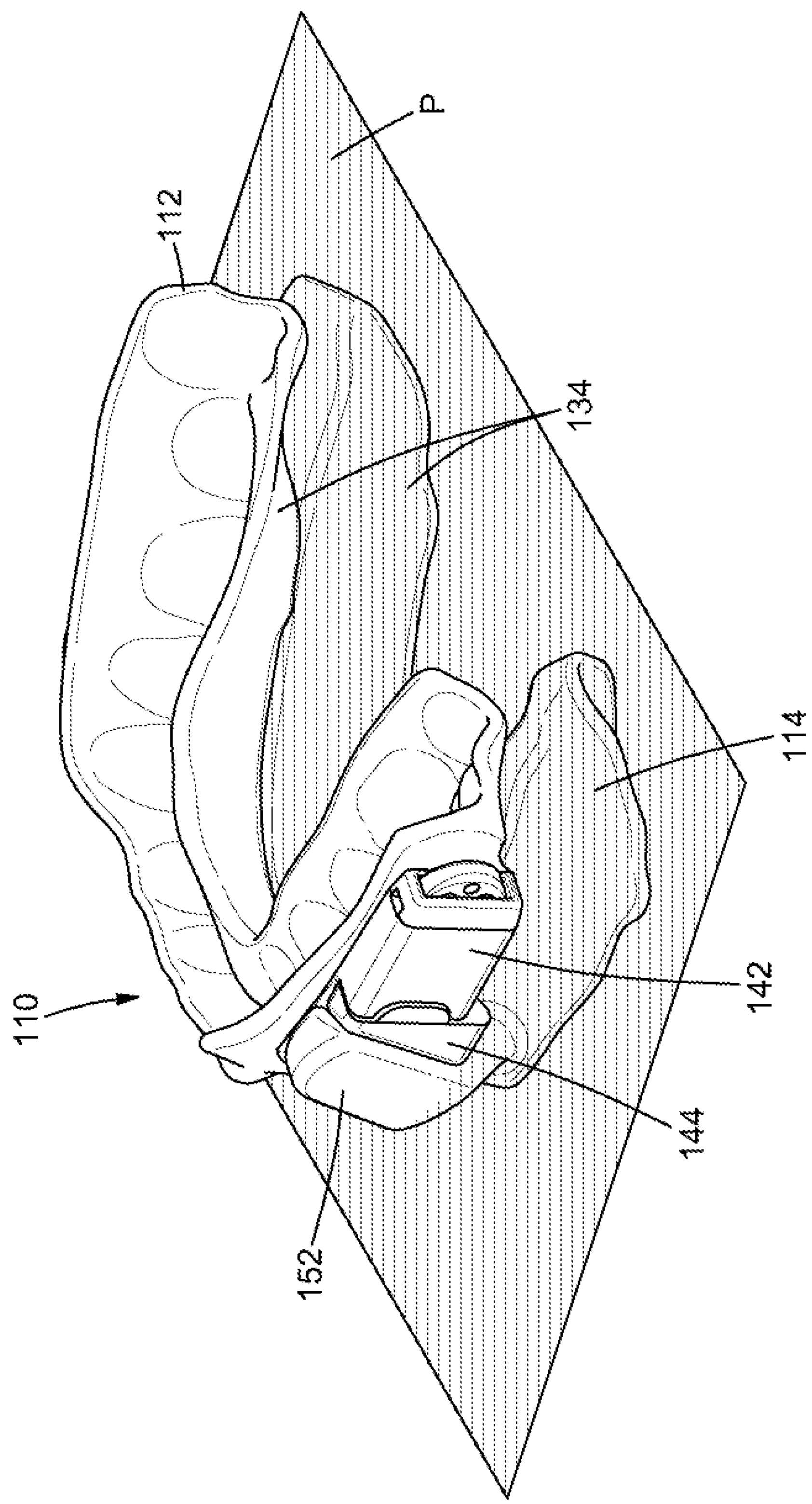
FIG. 7 is a perspective view of the set of occlusal splints of FIG. 6, wherein the maxillary splint and the mandibular splint are shown in a contact configuration.
Figure 8:
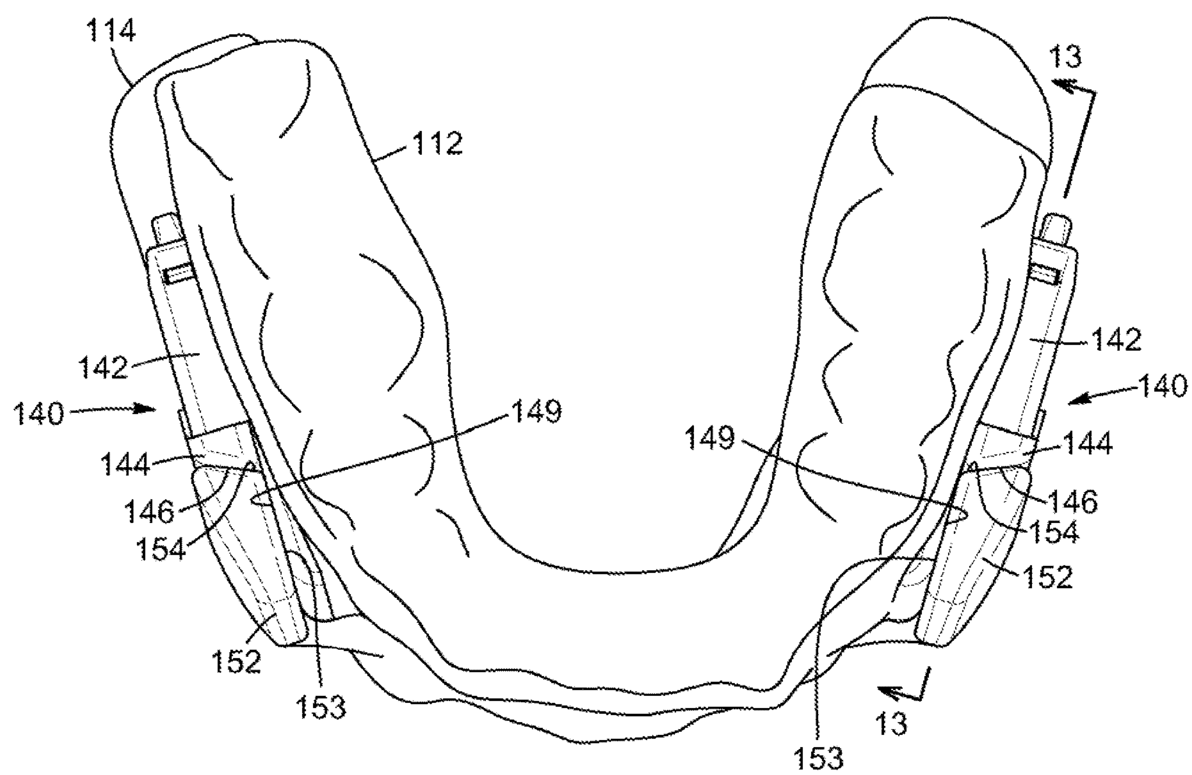
FIG. 8 is a top view of the set of occlusal splints of FIG. 6, wherein the maxillary splint and the mandibular splint are shown in a contact configuration.
Figure 9:
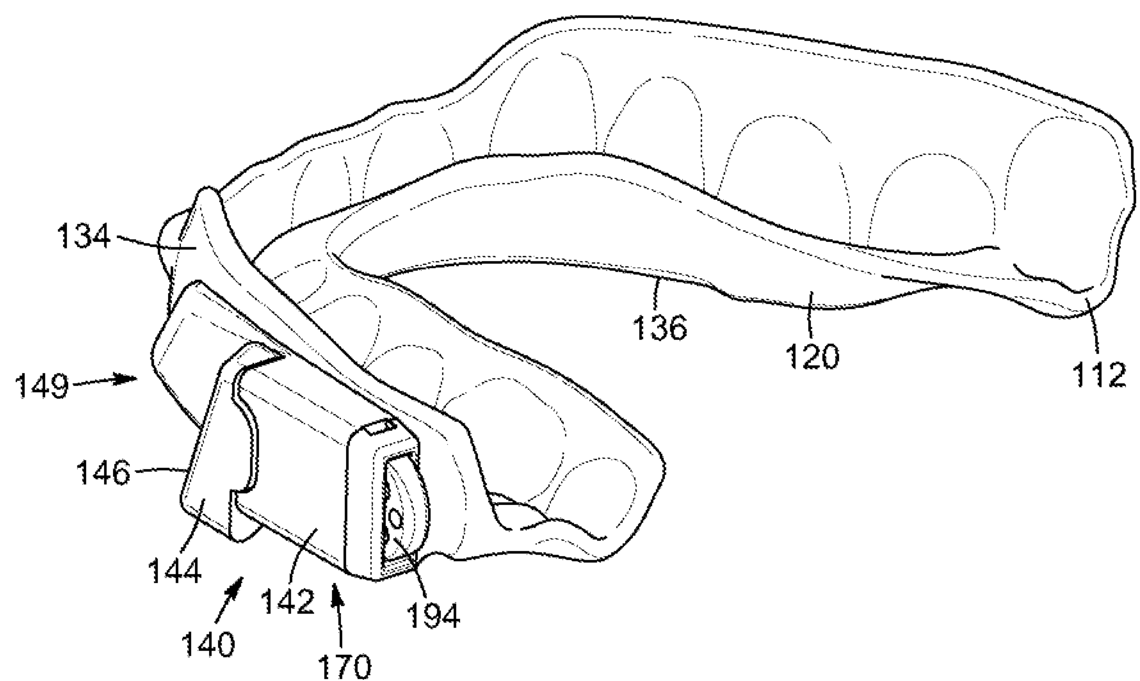
FIG. 9 is a perspective view of the mandibular splint of the set of occlusal splints of FIG. 6, wherein an advancement adjustment structure is shown.
Figure 13:
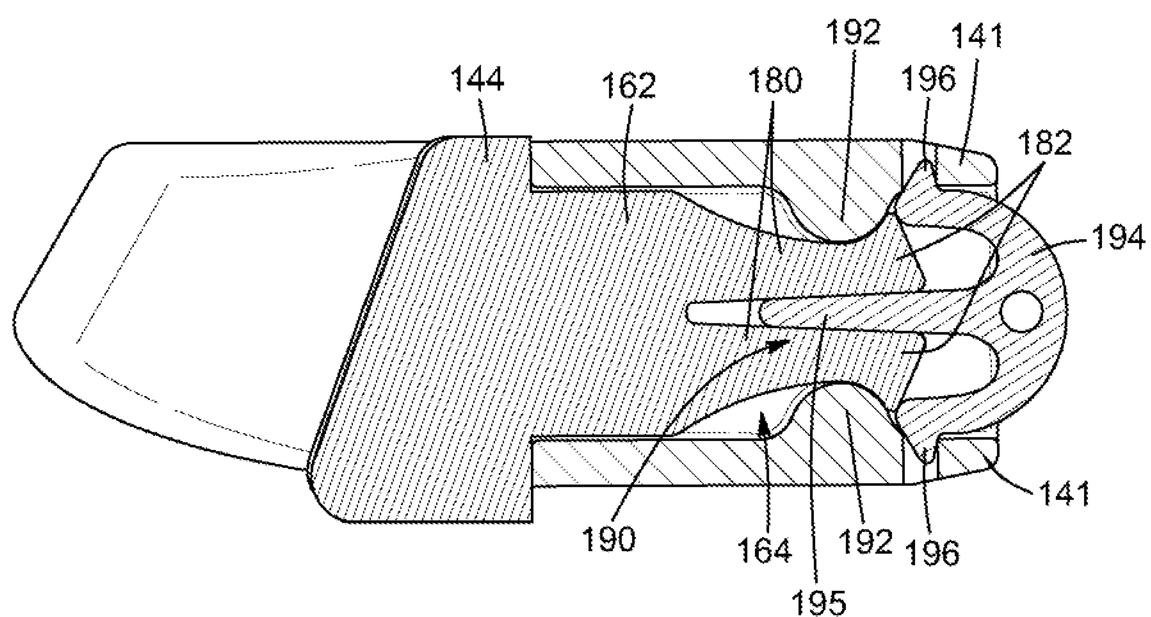
FIG. 13 is a cross-sectional view of a portion of the connecting assembly an abutment spacer of the set of occlusal splints of FIG. 6, taken along lines 13-13 in FIG. 9.

One skilled in the art will understand that, in other alternative embodiments, the adjustment spacer 44 can be removably connected to the corresponding support bracket 42 through connecting assemblies 60 having a different configuration than the ones of the embodiment shown and described above with reference to FIGS. 4 and 5. For example and without being limitative, an alternative embodiment of a connecting assembly 60 is shown in FIGS. 6, 9 and 13 and will be described in more details below. Moreover, in other alternative embodiments (not shown), the adjustment spacer 44 and support bracket 42 can engage in a taper configuration, wherein one of the protrusion 62 and receiving cavity 64 has a tapered configuration to gradually increase the friction fit therebetween during engagement, the adjustment spacer 44 and support bracket 42 can be screwed to one another, or the like.

Moreover, in other alternative embodiments, the connecting assembly 60 can have a different configuration than the male-female connecting assembly of the embodiment shown and described above in connection to FIGS. 1 to 5. For example and without being limitative, the protrusion 62 can project from the support bracket 42 (or be embodied by the support bracket 42) while the receiving cavity 64 can be defined in a body of the adjustment spacer 44, the protrusion 62 and complementary receiving cavity 64 can be located along inner and outer side walls of the adjustment spacer 44 and support bracket 42 respectively, or the like. Moreover, in other alternative embodiments (not shown), the connecting assembly 60 for removably connecting the adjustment spacer 44 to the corresponding support bracket 42 can differ from a male-female assembly and the adjustment spacer 44 can be removably connected to the corresponding support bracket 42 by any fastening or securing mean or method, such as, clipping, friction fit, or the like.

In view of the above, in the embodiment shown in FIGS. 1 to 5, the mandibular advancement provided by the maxillary splint 12 and the mandibular splint 14 can be modified (or adjusted) through replacement of the adjustment spacers 44 with adjustment spacers having a different spacing length 47 (i.e. a spacing length greater or smaller than the previously mounted adjustment spacers 44). In the embodiment shown, the spacing length 47 of the adjustment spacers 44 can be defined as the distance between the posterior wall 48 of the adjustment spacers 44 and the abutment surface 46 thereof. One skilled in the art will however understand that, in alternative embodiments (not shown), the spacing length 47 of the adjustment spacers 44 can be defined by the distance between the abutment surface 46 and a support bracket engaging portion of the adjustment spacers 44 different from the posterior wall 48. In other words, the spacing length 47 of the adjustment spacers 44 is defined by a distance between the abutment surface 46 and a section of the adjustment spacers 44 engaged to the maxillary splint 12, when the adjustment spacers 44 are mounted thereto, and which defines the mandibular advancement provided by the maxillary splint 12 and the mandibular splint 14.

In the embodiment shown in FIGS. 1 to 5, where the abutment surface 46 is forwardly angled, thereby resulting in adjustment spacers 44 having a substantially trapezoidal shape, the spacing length 47 should always be measured at a substantially similar position, for example along and/or parallel to a lower end or an upper end thereof. For example and without being limitative, in the embodiment shown, the spacing length 47 is measured at a lower end of the adjustment spacers 44.

Using the above-described set of maxillary splint 12 and mandibular splint 14, in an embodiment, the splint 12, 14 can be adjusted to reach an appropriate mandibular advancement for the patient. For example, in an embodiment, adjustment spacers 44 of an initial spacing length can be used (i.e. adjustment spacers 44 of the initial spacing length can be secured to the support bracket 42 of the maxillary splint 12) and the set of maxillary splint 12 and mandibular splint 14 can be tested by the patient to determine if the mandibular advancement is appropriate. If the mandibular advancement is not appropriate, adjustment spacers 44 of a different spacing length can successively be fitted onto the maxillary splint, until the maxillary splint 12 and mandibular splint 14 provide the appropriate mandibular advancement. In the context of the present description, the terms "testing" the set of maxillary splint 12 and mandibular splint 14 and "determine if the mandibular advancement is appropriate" can encompass any method for concluding on whether the mandibular advancement provided by the maxillary splint 12 and mandibular splint 14 is adapted to the patient. For example and without being limitative, it can include having the patient wearing the set of splints 12, 14 over a sufficient time period to determine whether the current mandibular advancement provided by the set of splints 12, 14 causes pain or not.

In an embodiment, the initial spacing length of the adjustment spacers 44 provides an initial mandibular advancement. For example and without being limitative, in an embodiment, the initial mandibular advancement corresponds to about 70% of the maximal mandibular advancement of the patient.

If the initial mandibular advancement provided by the adjustment spacers 44 of the initial spacing length is insufficient (or smaller than the desired mandibular adjustment), adjustment spacers 44 of longer lengths, such as for example and without being limitative adjustment spacers 44 each having a length between about 0.1 millimeter and about 1 millimeter more can successively be secured to the corresponding one of the splints 12, 14 (with the set of splints 12, 14 being tested by the patient for each successive try) until the splints 12, 14 provide the appropriate mandibular advancement. In an embodiment, adjustment spacers 44 each having a length of about 0.5 more millimeter can successively be secured to the corresponding one of the splints 12, 14 (with the set of splints 12, 14 being tested by the patient for each successive try) until the splints 12, 14 provide the appropriate mandibular advancement.

Conversely, if the initial mandibular advancement provided by the adjustment spacers 44 of the initial spacing length is too great, adjustment spacers 44 of a shorter length, such as for example and without being limitative adjustment spacers 44 having a length between about 0.1 millimeter and about 1 millimeter less can successively be used (with the set of splints 12, 14 being tested by the patient for each successive try) until the splints 12, 14 provide the appropriate mandibular advancement. In an embodiment, adjustment spacers 44 each having a length of about 0.5 less millimeter can successively be secured to the corresponding one of the splints 12, 14 (with the set of splints 12, 14 being tested by the patient for each successive try) until the splints 12, 14 provide the appropriate mandibular advancement.

One skilled in the art will understand that, using the above described set of splints 12, 14, if, at any point, the successive replacement of the adjustment spacers 44 results in a mandibular adjustment that is too great, adjustment spacers 44 of a shorter length (for example, the previously tested adjustment spacers 44) can be used to return to a smaller mandibular adjustment. Conversely, if at any point the successive replacement of the adjustment spacers 44 results in a mandibular adjustment that is too small, adjustment spacers 44 of a longer length (for example, the previously tested adjustment spacers 44) can be used to return to a greater mandibular adjustment. Hence, the above-described set of splints 12, 14, allows forward and rearward adjustment of the mandibular adjustment provided by the splints 12, 14, as the different adjustment spacers 44 can be secured and unsecured from the corresponding support bracket as needed.

Referring again to FIG. 5, in an embodiment, there is therefore provided a set of removable adjustment spacers 44 removably connectable to an outer portion of the maxillary splint 12 or the mandibular splint 14 of the set of mandibular advancement splints 12, 14. The set of removable adjustment spacers 44 comprises removable adjustment spacer 44 of a specific spacing length 47 and similar to the above described adjustment spacers 44. Each adjustment spacer 44 of the set has the same specific spacing length 47. In the embodiment shown in FIGS. 1 to 4, the set of removable adjustment spacers 44 comprises two adjustment spacers 44 of the specific spacing length 47, each connectable to an outer portion of the maxillary splint 12 of the set of mandibular advancement splints 12, 14, on a respective side thereof. In alternative embodiments (not shown), the set of removable adjustment spacers 44 could include a single adjustment spacer 44 or more than two adjustment spacers 44, the amount of adjustment spacers 44 of the set of removable adjustment spacers 44 corresponding to the amount of adjustment spacers 44 to be mounted to the outer portion of the maxillary splint 12 or the mandibular splint 14 of the set of mandibular advancement splints 12, 14 to provide the mandibular advancement.

Each removable adjustment spacer 44 of the set of removable adjustment spacers 44 comprises a body having the specific spacing length 47 defining the mandibular advancement provided by the set of mandibular advancement splints, 12, 14 and a connecting assembly 60 for removably securing the adjustment spacers 44 to the outer portion of the corresponding one of the maxillary splint 12 and the mandibular splint 14.

As mentioned above, in the embodiment shown in FIGS. 1 to 4, each one of the adjustment spacers 44 is configured to be removably secured to a corresponding one of the at least one support bracket 42 projecting from the outer wall surface 34 of the corresponding one of the maxillary splint 12 and the mandibular splint 14. One skilled in the art will understand that, in an alternative embodiment (not shown), each one of the adjustment spacers 44 can however be configured to be removably secured to the outer portion 32 of the corresponding one of the maxillary splint 12 and the mandibular splint 14, differently than through a support bracket 42.

In an embodiment, there is further provided a kit of adjustment spacers 44 including at least two sets of removable adjustment spacers 44 removably connectable to an outer portion of the maxillary splint 12 or mandibular splint 14 of the set of mandibular advancement splints 12, 14. Each set of removable adjustment spacers 44 of the kit of adjustment spacers 44 comprises at least one removable adjustment spacer 44 of a specific spacing length 47. Once again, if the set of removable adjustment spacers 44 includes more than one adjustment spacer 44, each adjustment spacer 44 of the set has the same specific spacing length 47. The adjustment spacers 44 of each set of removable adjustment spacers 44 of the kit of adjustment spacers 44 have a different spacing length 47, such that the adjustment spacers 44 of each set of removable adjustment spacers 44 can be mounted to the corresponding one of the maxillary splint 12 and the mandibular splint 14 to vary the mandibular adjustment provided by the splints 12, 14.

In an embodiment, there is further provided a mandibular advancement kit including the above-described set of maxillary splint 12 and mandibular splint 14 and the above-described kit of adjustment spacers 44 including a plurality of sets of removable adjustment spacers 44.

Referring to FIGS. 6 to 10, there is shown an alternative embodiment of a set of mandibular advancement splints 110, wherein similar features are numbered using the same reference numerals in the 100 series. The set of mandibular advancement splints 110 again includes a maxillary splint 112 engageable over the maxillary dental arch of the patient (not shown) and a mandibular splint 114 engageable over the mandibular dental arch of the patient (not shown). The body 120 of the maxillary splint 112 and the mandibular splint 114 is substantially similar to the above described body of the maxillary splint 12 and mandibular splint 14 of the embodiment of FIGS. 1 to 4 and also includes contact sections 136 abutting along a contact plane P, when the maxillary splint 112 and the mandibular splint 114 are configured in the contact configuration (see FIG. 7).

The maxillary splint 112 and the mandibular splint 114 again respectively include a maxillary abutment assembly 140 and a complementary mandibular abutment assembly 150 sized and shaped to abut against one another when the splints 112, 114 are configured in the contact configuration and cooperating to provide the desired mandibular advancement. The mandibular abutment assembly 150 of the mandibular splint 114 again includes two projections 152 extending upwardly from the outer wall surface 134 and positioned on opposite sides of the mandibular splint 114, outwardly of the contact section 136 of the outer wall surface 134 of the mandibular splint 114. Each one of the projections 152 again includes an abutment surface 154 configured to abut with the abutment surface of the components of the maxillary abutment assembly 140. Similarly to the above described embodiment of FIGS. 1 to 4, at least a section of the abutment surface 154 of each one of the projections 152 is located above the contact plane P, but one skilled in the art will understand that the abutment surface 154 of each one of the projections 152 could extend at least partially below the contact plane P.

Once again, the maxillary abutment assembly 140 of the maxillary splint 112 includes an advancement adjustment structure 170 with two support brackets 142 projecting outwardly from the outer wall surface 134, on opposite sides of the maxillary splint 112, and superposed thereto; and two adjustment spacers 144 removably securable to a corresponding one of the support brackets 142. Each adjustment spacer 144 includes an abutment surface 146 at least partially abuttable against the abutment surface 154 of the corresponding projection 152 of the mandibular abutment assembly 150, when the splints 112, 114 are configured in the contact configuration (See FIG. 7). As mentioned above, in alternative embodiments, assemblies different than the embodiment shown can be used for the mandibular abutment assembly 150 and maxillary abutment assembly 140.

In the embodiment shown in FIGS. 6 to 10, the abutment surface 146, 154 of each one of the adjustment spacers 144 and projections 152 have complementary rearward inclinations (or angular orientations). In other words, an upper end of the abutment surfaces 146, 154 of each one of the adjustment spacers 144 and the projections 152 extends rearwardly further than a lower end thereof, thereby defining a rearwardly angled surface. As mentioned above, one skilled in the art will however understand that, in alternative embodiments, the abutment surface 146, 154 of each one of the adjustment spacers 144 and projections 152 could have complementary forward inclinations (or angular orientations) (see FIG. 2) or could have substantially no inclination.

In the embodiment shown in FIGS. 6 to 10, the abutment surface 146, 154 of each one of the adjustment spacers 144 and projections 152 have complementary inward inclination (or angular orientations). In other words, an outer end of the abutment surfaces 146, 154 of each one of the adjustment spacers 144 and the projections 152 extends rearwardly further than an inner end thereof, thereby defining an inwardly angled surface. The complementary inward inclination (or angular orientations) of the abutment surface 146, 154 of each one of the adjustment spacers 144 and projections 152 helps to center the maxillary splint 112 with regard to the mandibular splint 114, when the splints 112, 114 are configured in the contact configuration and therefore minimize patient pain or discomfort which can be caused by improper positioning thereof due to jaw movement of the patient when the splints are worn. One skilled in the art will however understand that, in alternative embodiments, the abutment surface 146, 154 of each one of the adjustment spacers 144 and projections 152 could have substantially no inward inclination (see for example FIGS. 1 to 5.).

Once again, to allow replacement (or substitution) of the adjustment spacers 144, each one of the adjustment spacers 144 is removably connected to the corresponding support bracket 142 through a detachable connecting assembly 160. In the embodiment shown in FIGS. 6 to 13, each one of the adjustment spacers 144 again includes a protrusion 162 engageable into the receiving cavity 164 of the support bracket 142. In the embodiment shown, the protrusion 162 includes two flexible branches 180 spaced apart from one another and each having a stop member 182 defined at a distal end thereof. One skilled in the art will however understand that, in an alternative embodiment, only one branch 180 with a stop member 182 could be provided. The receiving cavity 164 includes a narrow section 190 (i.e. a section wherein protuberances 192 extend into the receiving cavity 164, to provide therebetween a section narrower than the remaining portion of the receiving cavity 164). Therefore, when the adjustment spacer 144 is engaged with a corresponding support bracket 142 (through insertion of the protrusion 162 of the adjustment spacer 144 into the receiving cavity 164 of the support bracket 142), the adjustment spacer 144 and support bracket 142 engage in a snap fit configuration.

Indeed, during insertion of the protrusion 162 into the receiving cavity 164, the flexible branches 180 of the protrusion 162 are bended temporarily, as the stop members 182 move past the protuberances 192, and subsequently return substantially to their original configuration, thereby “locking” the stop member 182 past the protuberances 192. In other words, once the temporary bending of the flexible branches 180 of the protrusion 162 has allowed the stop members 182 to move past the protuberances 192, the protuberances 192 engage the stop members 182 and restrict the reverse movement of the protrusion 162. In order to disengage the adjustment spacer 144 from the corresponding support bracket 142, sufficient force to bend the branches 180 of the protrusion 162 must be applied for the stop members 182 to again move past the protuberances 192 (in the reverse direction).

In the embodiment shown, the stop member 182 and protuberances 192 each have bevelled (or rounded) edges to help the transition of the stop member 182 past the protuberances 192 during engagement/disengagement of the adjustment spacer 144 and the support bracket 142, but one skilled in the art will understand that, in alternative embodiments (not shown), other configurations to allow such transition can be provided.

In the embodiment shown, the connecting assembly 160 further includes a locking member 194 engageable with the protrusion 162 of a corresponding adjustment spacer 144 in order to lock the adjustment spacer 144 in the support bracket 142 (i.e. to lock the adjustment spacer 144 in an engagement configuration with the support bracket 142 (see FIG. 13)). The locking member 194 includes a locking pin 195 insertable between the two flexible branches 180 of the protrusion 162 of the adjustment spacer 144 and locking tabs 196 engageable with the support bracket to maintain the locking member 194 engaged therewith. Hence, in an embodiment, to lock the adjustment spacer 144 in an engagement configuration with the support bracket 142, the locking member 194 can be inserted in the receiving cavity 164 of the support bracket 142 from a rear end of the body of the support bracket 142, thereby inserting the locking pin 195 between the two flexible branches 180 of the protrusion 162 of the adjustment spacer 144 and preventing bending thereof to lock the adjustment spacer in place. When the locking member 194 is inserted in the receiving cavity 164 of the support bracket 142, sections of the locking member 194 can bend momentarily such that the locking tabs 196, move past abutment lips 141 extending into the receiving cavity 164 of the support bracket 142, at a rear end thereof, thereby maintaining the locking member 194 in place. Inversely, the locking member 194 can subsequently be removed by bending the locking tabs 196 to move past the abutment lips 141, in a rearward motion, to remove the locking pin 195 from between the two flexible branches 180 of the protrusion 162, before the adjustment spacer 144 can be disengaged from the support bracket 142.

In the embodiment shown in FIGS. 6 to 10, the maxillary abutment assembly 140 further includes a lateral support section 149 providing lateral support to the adjustment spacer 144, thereby preventing inward lateral movement of the adjustment spacer, in the eventuality of a lateral force being exerted thereon, when the set of splints 112, 114 is worn by a patient. The lateral support section 149 is a section of the outer wall surface 134 which is positioned and configured to abut at least partially with an inner surface of the adjustment spacer 144, to provide lateral support thereto. In the embodiment shown, the lateral support section 149 is a substantially flat section extending along a portion of the outer wall surface 134, forwardly of the support bracket 142.

In the embodiment shown, the lateral support section 149 and the projections 152 of the mandibular splint 114 are positioned and configured such that an inner surface 153 of the projections 152 can also abut against the lateral support section 149 of the maxillary abutment assembly 140, when the splints 112, 114 are in the contact configuration (for a specific mandibular abutment). Hence, the lateral support section 149 can also provide lateral support for the mandibular splint 114, and prevents or limits lateral movements of the mandibular splint 114 relative to the maxillary splint 112, in the eventuality of a lateral force being exerted onto the splints 112, 114, when worn by a patient (for example and without being limitative, as a result of sleep bruxism or the like).

Similarly to the above described embodiment of FIGS. 1 to 5, in the embodiment of FIGS. 6 to 10, the mandibular advancement provided by the maxillary splint 112 and the mandibular splint 114 can therefore be modified (or adjusted) through replacement of the adjustment spacers 144 with adjustment spacers having a different spacing length 147 (i.e. a spacing length greater or smaller than the previously mounted adjustment spacers 144). Hence, as described above, the splint 112, 114 can be adjusted to reach an appropriate mandibular advancement for the patient by successively securing adjustment spacers 144 of different spacing lengths 147 to the corresponding one of the splints 112, 114 (with the set of splints 112, 114 being tested by the patient for each successive try) until the splints 112, 114 provide the appropriate mandibular advancement. The above-described steps for the method of adjusting the mandibular advancement using the set of splints 112, 114 apply to the set of splints 112, 114 of the embodiment of FIGS. 6 to 10 and need not be repeated herein.

Referring to FIGS. 11 and 12, in an embodiment, a thickness 145 of the abutment surface 146 of the adjustment spacer 144 of a set of adjustment spacers 144 removably connectable to an outer portion of the maxillary splint 112 or the mandibular splint 114 of the set of mandibular advancement splints 112, 114 is adapted to provide a proper abutment between the abutment surface 146 of the adjustment spacer 144 and the corresponding projection 152. In other words, in an embodiment, the thickness 145 of the abutment surface 146 of the adjustment spacer 144 of a set of adjustment spacers 144 is adapted to the specific spacing length 147 of the adjustment spacer 144 of a set of adjustment spacers 144. In an embodiment, the thickness 145 of the abutment surface 146 of the adjustment spacer 144 of a set of adjustment spacers 144 having a longer spacing length 147 is greater than the thickness 145 of the abutment surface 146 of the adjustment spacer 144 of a set of adjustment spacers 144 having a shorter spacing length 147. Such adapted thickness 145 of the abutment surface 146 of the adjustment spacer 144 of a set of adjustment spacers 144 compensates for the lateral displacement of the corresponding projection 152 with regards to the abutment surface 146 of the adjustment spacer 144, when adjustment spacers 144 of different spacing length 147 are used. Indeed, given the U-shaped body 120 of the mandibular splint 114, the lateral alignment of the corresponding projection 152 with regards to the abutment surface 146 of the adjustment spacer 144 is varied depending on how much the mandibular splint 114 is driven forward with regard to the maxillary splint 112, to produce the desired mandibular advancement. Therefore, the increasing thickness 145 of the abutment surface 146 of the adjustment spacer 144 for adjustment spacers 144 having a greater spacing length 147 compensates the lateral displacement of the corresponding projection 152 and results in proper abutment between the abutment surface 146 of the adjustment spacer 144 and the corresponding projection 152 (i.e. a sufficient contact to provide a steady connection therebetween).

In view of the above, in an embodiment, the kit of adjustment spacers 144 including at least two sets of removable adjustment spacers 144 removably connectable to an outer portion of the maxillary splint 112 or mandibular splint 114 of the set of mandibular advancement splints 112, 114 includes sets of removable adjustment spacers 144 where the thickness 145 of the abutment surface 146 of the adjustment spacer 144 of a set of adjustment spacers 144 having a longer spacing length 147 is greater than the thickness 145 of the abutment surface 146 of the adjustment spacer 144 of a set of adjustment spacers 144 having a shorter spacing length 147.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

What is claimed is:

1. A set of mandibular advancement splints comprising:

a maxillary splint having a maxillary body with an inner portion adapted to fit a maxillary dental arch of a mouth of a patient and an opposed outer portion having an outer wall surface, the maxillary body having an anterior section and two posterior sections extending rearwardly from opposite ends of the anterior section, the maxillary splint having a maxillary abutment assembly; and a mandibular splint having a mandibular body with an inner portion adapted to fit a mandibular dental arch of the mouth of the patient and an opposed outer portion having an outer wall surface, the mandibular splint having a mandibular abutment assembly;

wherein the maxillary abutment assembly comprises:

support brackets, each one projecting outwardly from the outer wall surface of the outer portion of the maxillary body in the posterior sections thereof and extending between an anterior face and a posterior face;

lateral support sections, each one forming a thickened area disposed along the outer wall surfaces of the posterior sections; and adjustment spacers removably securable to a corresponding one of the support brackets and projecting forwardly from the anterior face of the corresponding one of support brackets when secured thereto, the adjustment spacers having an anterior face, an inner surface, and a posterior face with the posterior face abutting against the anterior face of the corresponding one of the support brackets, wherein the mandibular abutment assembly comprises:

projections extending upwardly from the outer wall surface of the mandibular body and having an inner surface, each one of the lateral support sections defining a substantially flat outer surface extending towards the anterior section of the maxillary body beyond the anterior face of the corresponding one of the support brackets, such that the substantially flat outer surface of the lateral support sections are configured to at least partially contact the inner surfaces of the corresponding one of the adjustment spacers and the inner surfaces of the corresponding projections to provide lateral support thereto;

wherein the adjustment spacers and the support brackets further comprise a complementary male-female connecting assembly including a receiving cavity defined in one of the adjustment spacers and the support brackets and a protrusion protruding from the other one of the adjustment spacers and the support brackets, the protrusion being engageable in the receiving cavity in a detachable snap-fit engagement.

2. The set of mandibular advancement splints of claim 1, wherein the receiving cavities are defined in the support brackets and the adjustment spacers comprise the protrusions extending from the posterior face thereof.

3. The set of mandibular advancement splints of claim 1, wherein the support brackets comprise the receiving cavities and the support brackets further comprise protuberances extending into the receiving cavities to define a narrow section therein, and wherein the adjustment spacers comprise the protrusions, each one of the protrusions including two flexible branches spaced apart from one another and each one of the flexible branches having a stop member provided at a distal end, the protrusions being insertable into the receiving cavity of the corresponding one of the support brackets from a first side thereof with the stop members extending past the narrow section of the receiving cavity in an engagement configuration.

4. The set of mandibular advancement splints of claim 3, further comprising locking members engageable with the protrusion of a respective one of the adjustment spacers to lock the respective one of the adjustment spacers inside the receiving cavity of the corresponding one of the support brackets, each one of the locking members including a locking pin and locking tabs, each one of the locking members being insertable into the receiving cavity of the corresponding one of the support brackets from a second side thereof with the locking pin extending between the two flexible branches of the protrusion of the respective one of the adjustment spacers and the locking tabs engaged with the corresponding one of the support brackets.

5. The set of mandibular advancement splints of claim 2, wherein the maxillary splint and the mandibular splint are configurable in a contact configuration where contact sections thereof are abutted one against the other and extend along a contact plane, a portion of the adjustment spacers extends below the contact plane with a lower edge of the support brackets being at least one of substantially aligned with and extending above the contact plane when the maxillary splint and the mandibular splint are configured in the contact configuration.

6. The set of mandibular advancement splints of claim 2, wherein each one of the outer wall surface of the maxillary splint and the outer wall surface of the mandibular splint comprises a contact section and the lateral support sections extend upwardly from the contact section of the maxillary splint.

7. The set of mandibular advancement splints of claim 6, wherein the maxillary splint and the mandibular splint are configurable in a contact configuration where the contact sections thereof are abutted one against the other and extend along a contact plane and wherein each one of the projections comprises an abutment surface and the anterior face of the adjustment spacers defined a complementary abutment surface configured to abut with the abutment surface of a corresponding one of the projections, and the abutment surfaces of the adjustment spacers and the abutment surfaces of the projections being complementary in shape and inwardly inclined to define an oblique angle with the contact plane with the abutment surfaces of the adjustment spacers and the projections extending at least partially above the contact plane.

8. The set of mandibular advancement splints of claim 1, wherein each one of the adjustment spacers has a spacing length and a thickness, with the thickness being variable along the spacing length with the adjustment spacers being thicker adjacent the anterior face.

9. A set of mandibular advancement splints comprising:

a maxillary splint having a maxillary body with an inner portion adapted to fit a maxillary dental arch of a mouth of a patient and an opposed outer portion having an outer wall surface, the maxillary body having an anterior section and two posterior sections extending rearwardly from opposite ends of the anterior section, the maxillary splint having a maxillary abutment assembly comprising:

support brackets, each one having an anterior face facing anteriorly relative towards the anterior section, adjustment spacers, each one having a posterior face abutable against the anterior face of a respective one of the support brackets, and lateral support sections, each one forming a thickened area disposed along the outer wall surfaces of the posterior sections and having a substantially flat outer surface;

each one of the support brackets and the lateral support sections projection outwardly from the outer wall surface of the outer portion of the maxillary body, from a respective one of the posterior sections, each one of the lateral support sections extending towards the anterior section of the maxillary body beyond the anterior face of the corresponding one of the support brackets, each one of the support brackets having a thickness that is thicker than the thickened area of the corresponding one of the lateral support sections, the adjustment spacers being removably securable to a corresponding one of the support brackets and projecting forwardly form the anterior face thereof when secured thereto, each one of the adjustments spacers having an inner surface abutting the substantially flat outer surface of the corresponding one of the lateral support sections and being supported laterally thereby; and a mandibular splint having a mandibular body with an inner portion adapted to fit a mandibular dental arch of the mouth of the patient and an opposed outer portion having an outer wall surface, the mandibular splint having a mandibular abutment assembly wherein the maxillary abutment assembly and the mandibular abutment assembly.

10. The set of mandibular advancement splints of claim 9, wherein each one of the adjustment spacers comprises two flexible branches spaced apart from one another and having a stop member provided at a distal end and wherein each one of the support brackets comprises a receiving cavity defined therein and at least two protuberances extending into the receiving cavity to define a narrow section in the receiving cavities, the flexible branches being removably insertable into the receiving cavity of the corresponding one of the support brackets from a first side thereof with the stop members extending past the narrow section of the receiving cavity in an engagement configuration for selectively and removably securing each one of the adjustment spacers to the corresponding one of the support brackets into a detachable snap-fit engagement.

11. The set of mandibular advancement splints of claim 10, further comprising locking members engageable with the flexible branches of a respective one of the adjustment spacers to lock the respective one of the adjustment spacers inside the receiving cavity of the corresponding one of the support brackets, each one of the locking members including a locking pin and locking tabs, each one of the locking members being insertable into the receiving cavity of the corresponding one of the support brackets from a second side thereof with the locking pin extending between the two flexible branches of the respective one of the adjustment spacers and the locking tabs engaged with the corresponding one of the support brackets.

12. The set of mandibular advancement splints of claim 9, wherein the maxillary splint and the mandibular splint are configurable in a contact configuration where contact sections thereof are abutted one against the other and extend along a contact plane, a portion of the adjustment spacers extends below the contact plane with a lower edge of the support brackets being at least one of substantially aligned with and extending above the contact plane when the maxillary splint and the mandibular splint are configured in the contact configuration.

13. The set of mandibular advancement splints of claim 9, wherein lateral support sections form a thickening of the outer portion of the maxillary body, each one being thicker adjacent to the anterior section than rearwardly thereof, and wherein the mandibular abutment assembly comprises two projections extending upwardly from the outer wall surface, on opposed sides of the mandibular body of the mandibular splint and having an inner surface; wherein the substantially flat outer surface of each one of the lateral support sections is configured to at least partially contact with the inner surfaces a of corresponding one of the adjustment spacers and the projections to provide lateral support thereto.

14. The set of mandibular advancement splints of claim 13, wherein each one of the outer wall surface of the maxillary splint and the outer wall surface of the mandibular splint comprises a contact section, wherein each one of the adjustment spacers and the projections comprises an abutment surface with the abutment surface of the adjustment spacers being located at an anterior face thereof and being configured to abut with the abutment surface of a corresponding one of the projections and the abutment surfaces of the adjustment spacers and the abutment surfaces of the projections being complementary in shape and inwardly inclined to define an oblique angle with the substantially flat surface of a corresponding one of the lateral support sections, and wherein the maxillary splint and the mandibular splint are configurable in a contact configuration where the contact sections thereof are abutted one against the other and extend along a contact plane with the abutment surfaces of the adjustment spacers and the projections extending at least partially above the contact plane.

15. The set of mandibular advancement splints of claim 9, wherein each one of the adjustment spacers has a spacing length and an abutment surface extending forwardly when a corresponding one of the adjustment spacers is removably secured to the one of the maxillary splint and the mandibular splint, wherein a thickness of the adjustment spacers is variable along the spacing length with the adjustment spacers being thicker adjacent the abutment surfaces.

16. A set of mandibular advancement splints comprising:

a maxillary splint having a maxillary body with an inner portion adapted to fit a maxillary dental arch of a mouth of a patient and an opposed outer portion having an outer wall surface, the maxillary body having an anterior section and two posterior sections extending rearwardly from opposite ends of the anterior section, the maxillary splint having a maxillary abutment assembly; and a mandibular splint having a mandibular body with an inner portion adapted to fit a mandibular dental arch of the mouth of the patient and an opposed outer portion having an outer wall surface, the mandibular splint having a mandibular abutment assembly;

wherein the maxillary abutment assembly comprises:

support brackets, each one projecting outwardly from a respective side of the outer portion of the maxillary body in the posterior sections thereof;

lateral support sections, each one forming a thickened area disposed along the outer wall surfaces of the posterior sections, each one of the lateral support sections having an outer face with a substantially flat surface extending towards the anterior section of the maxillary body beyond an anterior face of a corresponding one of the support brackets; and at least two adjustment spacers removably securable to a corresponding one of the support brackets with a posterior face thereof abutted against the anterior face of the corresponding one of the support brackets and projecting forwardly therefrom when secured to the support brackets, wherein each one of the adjustment spacers has a spacing length and an abutment surface extending forwardly when secured to the corresponding one of the support brackets.

17. The set of mandibular advancement splints of claim 16, wherein the mandibular abutment assembly comprises projections extending upwardly from the outer wall surface of the mandibular splint, each one of the support brackets, the lateral support sections, and the projections projecting from a respective side of the outer portion of the mandibular body, each one of the lateral support sections being configured to at least partially contact with an inner surface of the corresponding ones of the adjustment spacers and the projections to provide lateral support thereto.

18. The set of mandibular advancement splints of claim 16, wherein the at least two adjustment spacers and the support brackets further comprise a complementary male-female connecting assembly including a receiving cavity defined in the support brackets and a protrusion protruding from each one of the at least two adjustment spacers, the protrusion being engageable in the receiving cavity in a detachable snap-fit engagement.

19. The set of mandibular advancement splints of claim 18, wherein each one of the adjustment spacers comprises the protrusion and each one of the support brackets comprises the receiving cavity and each one of the support brackets further comprises at least one protuberance extending into the receiving cavity, wherein the protrusion of the adjustment spacers is selectively and removably insertable into the receiving cavity of the corresponding one of the support brackets from a first side thereof, with the at least one protuberance engaging the inserted protrusion for selectively and removably securing each one of the adjustment spacers to the corresponding one of the support brackets into the detachable snap-fit engagement.

20. The set of mandibular advancement splints of claim 17, wherein the maxillary splint and the mandibular splint are configurable in a contact configuration where contact sections thereof are abutted one against the other and extend along a contact plane, a portion of the at least two adjustment spacers extends below the contact plane with a lower edge of the support brackets being at least one of substantially aligned with and extending above the contact plane when the maxillary splint and the mandibular splint are configured in the contact configuration.

* * * * *

UNITED STATES PATENT AND TRADEMARK OFFICE
CERTIFICATE OF CORRECTION

| | |
|---|---|
| PATENT NO. | : 11,278,444 B2 |
| APPLICATION NO. | : 16/678659 |
| DATED | : March 22, 2022 |
| INVENTOR(S) | : Gabriel Robichaud et al. |

It is certified that error appears in the above-identified patent and that said Letters Patent is hereby corrected as shown below:

In the Claims

Column 21, Lines 42-43, Claim 9:
After "mandibular splint having a mandibular abutment assembly"
Delete "wherein the maxillary abutment assembly and the mandibular abutment assembly."

Signed and Sealed this
Thirteenth Day of February, 2024

*Katherine Kelly Vidal*

Katherine Kelly Vidal
*Director of the United States Patent and Trademark Office*